(12) United States Patent
Rioux et al.

(10) Patent No.: US 8,216,235 B2
(45) Date of Patent: Jul. 10, 2012

(54) LIQUID INFUSION APPARATUS FOR RADIOFREQUENCY TISSUE ABLATION

(75) Inventors: Robert F. Rioux, Ashland, MA (US); Robert Garabedian, Tyngsboro, MA (US); Christopher Pearson, North Grafton, MA (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 1189 days.

(21) Appl. No.: 11/944,257

(22) Filed: Nov. 21, 2007

(65) Prior Publication Data

US 2008/0071266 A1    Mar. 20, 2008

Related U.S. Application Data

(62) Division of application No. 10/685,744, filed on Oct. 14, 2003, now abandoned.

(51) Int. Cl.
*A61B 18/14* (2006.01)
(52) U.S. Cl. ............................. 606/51; 606/41
(58) Field of Classification Search ............ 606/41, 606/45–52
See application file for complete search history.

(56) References Cited

U.S. PATENT DOCUMENTS

| | | | |
|---|---|---|---|
| 4,031,891 A | 6/1977 | Jess | |
| 4,512,768 A | 4/1985 | Rangaswamy | |
| 4,571,244 A | 2/1986 | Knighton | |
| 5,279,569 A | 1/1994 | Neer et al. | |
| 5,456,689 A | 10/1995 | Kresch et al. | |
| 5,484,436 A * | 1/1996 | Eggers et al. | 606/48 |
| 5,507,743 A | 4/1996 | Edwards et al. | |
| 5,643,197 A | 7/1997 | Bruker et al. | |
| 5,697,281 A | 12/1997 | Eggers et al. | |
| 5,697,882 A | 12/1997 | Eggers et al. | |
| 5,728,143 A | 3/1998 | Gough et al. | |
| 5,868,740 A | 2/1999 | Le Veen et al. | |
| 5,961,513 A | 10/1999 | Swanson et al. | |
| 6,017,338 A | 1/2000 | Brucker et al. | |
| 6,030,384 A * | 2/2000 | Nezhat | 606/48 |
| 6,050,992 A | 4/2000 | Nichols | |
| 6,071,280 A | 6/2000 | Edwards et al. | |
| 6,099,526 A | 8/2000 | Whayne et al. | |
| 6,210,411 B1 | 4/2001 | Hofmann et al. | |

(Continued)

FOREIGN PATENT DOCUMENTS

WO    WO 95/17222    6/1995

(Continued)

OTHER PUBLICATIONS

PCT International Search Report for PCT/US2004/032465, Applicant: Scimed Life Systems, Inc., Forms PCT/ISA/210 and 220, dated Mar. 14, 2005 (9 pages).

(Continued)

*Primary Examiner* — Michael Peffley
(74) *Attorney, Agent, or Firm* — Vista IP Lawgroup LLP

(57) ABSTRACT

An apparatus for delivering electrical energy includes a tubular member having a pair of opposing members extendable from the distal end of the tubular member, the opposing members being directable towards one another for engaging tissue between inner surfaces of the opposing members, the opposing members having one or more electrodes for delivering electrical energy to tissue engaged between the opposing members. One or more hollow needles extend from an inner surface of at least one opposing member, the hollow needles configured to deliver conductive fluid from a lumen into tissue penetrated by the needles.

11 Claims, 5 Drawing Sheets

U.S. PATENT DOCUMENTS

| | | |
|---|---|---|
| 6,212,433 B1 | 4/2001 | Behl |
| 6,217,554 B1 | 4/2001 | Green |
| 6,231,570 B1 | 5/2001 | Tu et al. |
| 6,235,022 B1 | 5/2001 | Hallock et al. |
| 6,235,023 B1 | 5/2001 | Lee et al. |
| 6,241,710 B1 | 6/2001 | VanTassel et al. |
| 6,277,115 B1 | 8/2001 | Saadat |
| 6,379,353 B1 | 4/2002 | Nichols |
| 6,425,887 B1 | 7/2002 | McGuckin et al. |
| 6,475,213 B1 | 11/2002 | Whayne et al. |
| 6,503,225 B1 | 1/2003 | Kirsch et al. |
| 6,610,060 B2 * | 8/2003 | Mulier et al. ............ 606/49 |
| 6,613,048 B2 * | 9/2003 | Mulier et al. ............ 606/49 |
| 6,716,211 B2 | 4/2004 | Mulier et al. |
| 7,387,628 B1 * | 6/2008 | Behl et al. ............ 606/41 |
| 2001/0001819 A1 | 5/2001 | Lee et al. |
| 2002/0120263 A1 * | 8/2002 | Brown et al. ............ 606/41 |
| 2002/0183638 A1 | 12/2002 | Swanson |
| 2003/0078573 A1 | 4/2003 | Truckai et al. |
| 2004/0215185 A1 | 10/2004 | Truckai et al. |
| 2005/0055019 A1 | 3/2005 | Skarda |
| 2005/0059964 A1 | 3/2005 | Fitz |

FOREIGN PATENT DOCUMENTS

| | | |
|---|---|---|
| WO | WO 96/29946 A1 | 10/1996 |
| WO | WO 00/35530 | 6/2000 |
| WO | WO 02/089686 A1 | 11/2002 |

OTHER PUBLICATIONS

PCT International Search Report for PCT/US2005/000483, Applicant: Scimed Life Systems, Inc., Forms PCT/ISA/201 and 220, dated Apr. 14, 2005 (7 pages).

PCT International Search Report for PCT/US2005/000483, Applicant: Scimed Life Systems, Inc., Forms PCT/ISA/210 and 220, dated Apr. 14, 2005 (4 pages).

Ahmed, Muneeb, MD, et al., "Improved Coagulation with Saline Solution Pretreatment during Radiofrequency Tumor Ablation in a Canine Model", J. Vasc Interv Radiol 2002; 13; 717-724.

Boehm, Thomas, M.D., et al., Radio-frequency Tumor Ablation: Internally Cooled Electrode versus Saline-enhanced Technique in an Aggressive Rabbit Tumor-Model Radiology 2002; 222; 805-813.

* cited by examiner

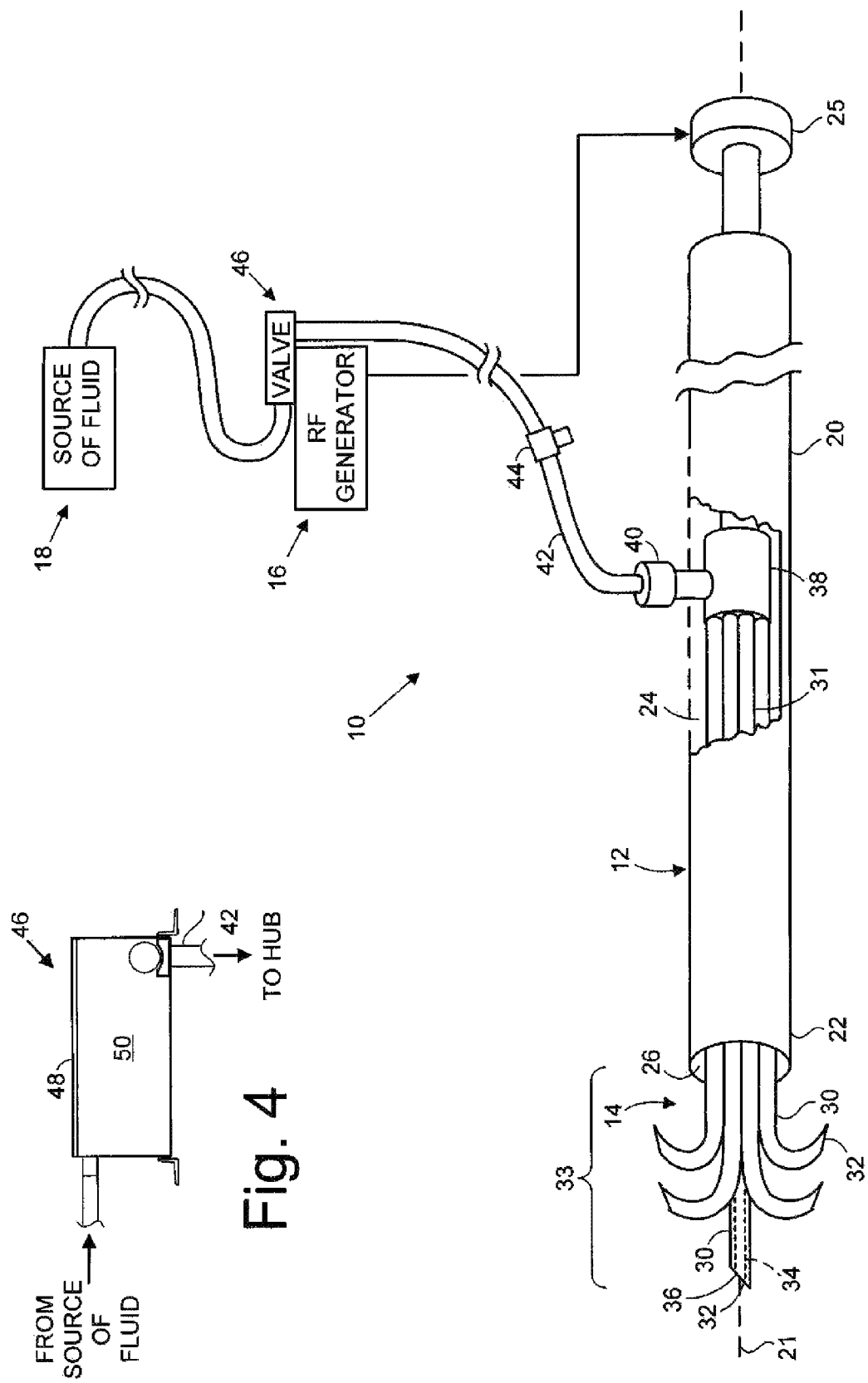

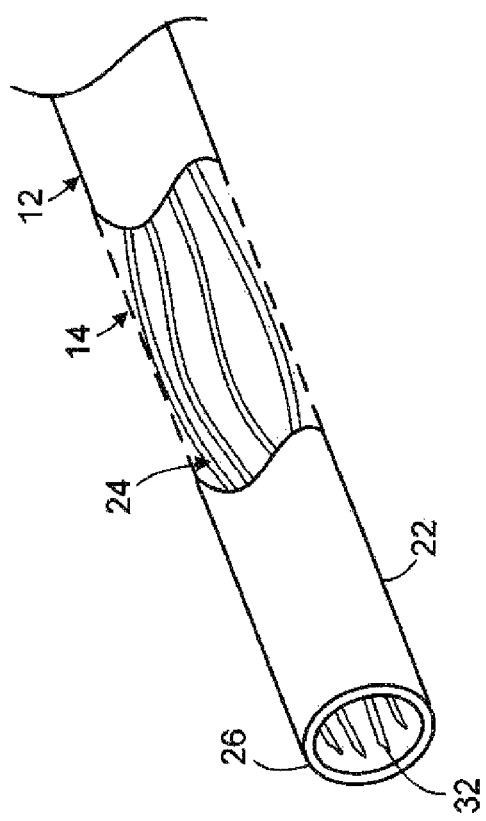
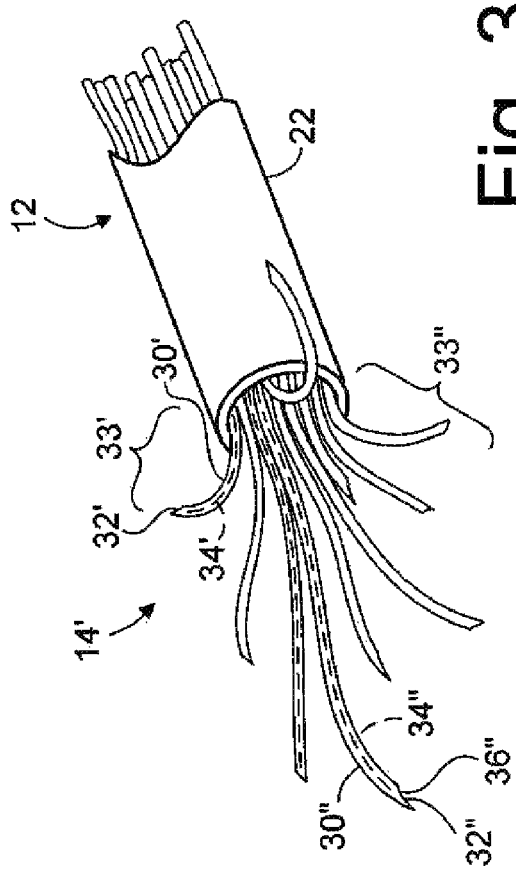

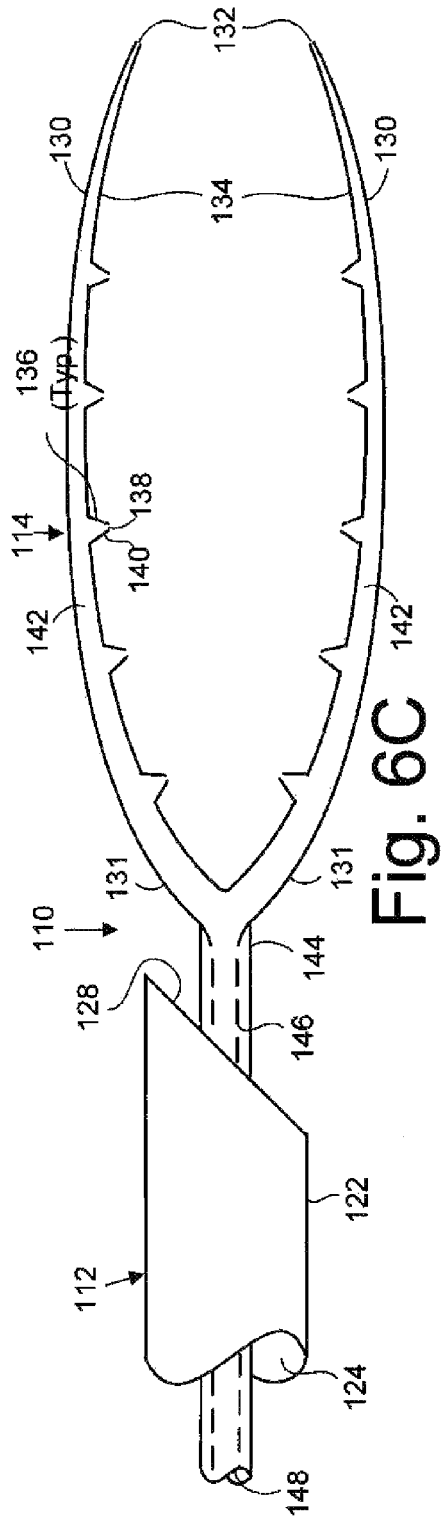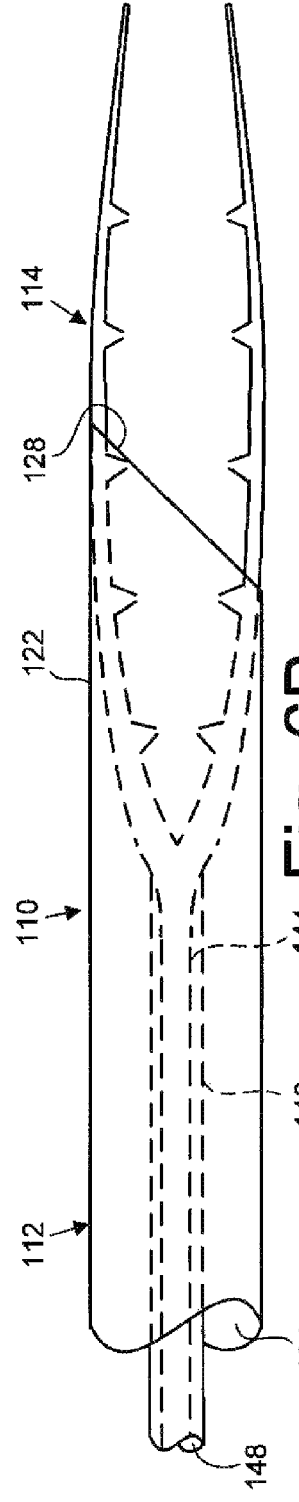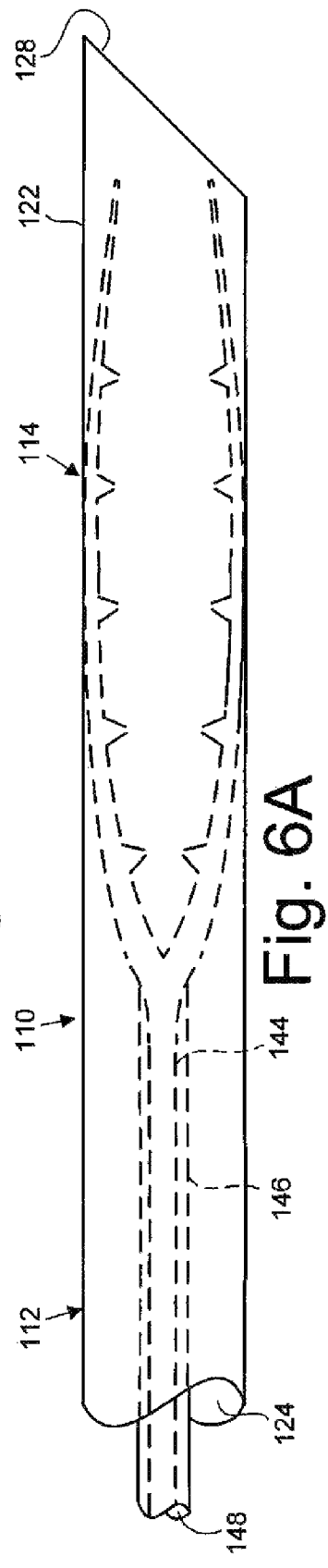

LIQUID INFUSION APPARATUS FOR RADIOFREQUENCY TISSUE ABLATION

RELATED APPLICATION DATA

This application is a divisional application of U.S. patent application Ser. No. 10/685,744, filed on Oct. 14, 2003, now abandoned, the contents of which are incorporated herein by reference as though set forth in full.

FIELD OF INVENTION

The present invention relates generally to apparatus for infusing fluids into tissue, such as a tumor, to enhance thermal heating and ablation of the tissue using radio frequency electrical energy.

BACKGROUND

Electrosurgical instruments for delivering radio frequency (RF) electrical energy into solid tissue are known. For example, published PCT application WO 96/29946 discloses electrosurgical probes that include a number of independent wire electrodes that may be extended into tissue from the distal end of a cannula. The electrodes may be energized in a monopolar or bipolar manner to heat and necrose a target tissue region. Such probes have been suggested for treating tumors within organs, such as the liver, kidney, pancreas, stomach, and spleen.

To enhance heating and necrosis, saline may be injected into the target region before delivering electrical energy. Generally, this involves advancing a needle from a syringe into the tissue before or after advancing the electrodes from an electrosurgical probe into the target region. Saline may be delivered from the syringe into the tissue through the needle, and then the electrodes may be energized to deliver RF energy and necrose tissue within the target region. Alternatively, saline may be delivered through a lumen in one or more of the wire electrodes. Saline may increase heating of the tissue, thereby increasing the size of the resulting lesion, as compared to energizing the electrodes without saline.

Because of inhomogeneities in the tissue of the target region, however, the saline injected by the syringe may not be perfused into the target region in a desired manner. For example, the saline may be perfused into tissue away from the electrodes, or only locally within a portion of the target region. Thus, the tissue within the target region may not be uniformly heated and necrosed as desired, possible requiring multiple treatments to ensure that the target region is successfully necrosed. In addition, where a separate syringe is used to deliver the saline, the syringe and probe require separate approaches into the tissue, complicating access and creating multiple tracks through the intervening tissue that may need to be closed and allowed to heal.

SUMMARY OF THE INVENTION

In accordance with one aspect of the invention, an apparatus is provided for delivering electrical energy to tissue within a patient, the apparatus including a tubular member having a proximal end, a distal end sized for insertion into a body of a patient and a lumen extending from the distal end towards the proximal end. In one embodiment, the tubular member may be a substantially rigid cannula having a sharpened distal tip for advancing the cannula through tissue.

One or more needles are extendable from the lumen beyond the distal end of the tubular member, each needle having a distal tip for penetrating tissue. At least one (and preferably all) of the one or more needles has an infusion lumen for delivering fluid to an outlet in its distal tip. In addition or alternatively, at least a distal portion of the needle(s) may be formed from a porous material, e.g., a sintered stainless steel. A source of conductive fluid, e.g., saline, are connected to the infusion lumen and/or porous material of the respective needle(s) for delivering the fluid to tissue beyond the distal tip(s) thereof.

In embodiments of the invention, the needle(s) are electrodes for delivering electrical energy to tissue adjacent the distal tip. For example, a distal portion of the needle(s) may include a conductive region defining an electrode. Preferably, the needle(s) are formed from electrically conductive material such that an exposed portion of each needle forms an electrode. A source of electrical energy, e.g., an RF generator, is coupled to the one or more needles in a monopolar or bipolar configuration, for delivering electrical energy to tissue surrounding the needle(s) when deployed in a patient.

The needle(s) are preferably movable from a retracted configuration within the lumen of the tubular member to an extended configuration, wherein distal portion(s) of the needle(s) extend beyond the distal end of the tubular member. In a preferred embodiment, a plurality of the needles are provided having distal tips that extend at different axial and radial distances from one another in the extended configuration, thereby defining a spherical or other three-dimensional shape in the expanded configuration.

In accordance with another aspect of the present invention, an apparatus is provided for delivering electrical energy to tissue within a patient that includes a tubular member having a proximal end, a distal end sized for insertion into a body of a patient, and a lumen extending between the proximal and distal ends. A plurality of opposing members are extendable from the distal end of the tubular member, the opposing members being extendable away from one another and directable towards one another for engaging tissue between inner surfaces of the opposing members.

The opposing members include one or more electrodes for delivering electrical energy to tissue engaged between the opposing members. One or more hollow needles extend from an inner surface of at least one, and preferably each, of the opposing members. Each needle may include a sharpened tip for penetrating tissue engaged between the opposing members and an outlet in the sharpened tip communicating with a lumen in the opposing member for delivering conductive fluid from the lumen into tissue penetrated by the sharpened tip. A source of electrical energy may be coupled to the electrodes for delivering electrical energy to ablate tissue engaged between the opposing members.

In one embodiment, the opposing members may extend from a control member extending through the lumen of the tubular member. The opposing members may be directable towards one another by directing the control member proximally to at least partially withdraw the opposing members into the lumen. In addition, the control member may include an infusion lumen communicating with the outlets of the needles. A source of conductive fluid may communicate with the infusion lumen for delivering conductive fluid to the outlets of the needles.

Other objects and features of the invention will become apparent from consideration of the following description taken in conjunction with the accompanying drawings.

BRIEF DESCRIPTION OF THE DRAWINGS

The drawings illustrate the design and utility of preferred embodiments of the invention, in which similar elements are referred to by common reference numerals, and in which:

FIG. 1 is a side view of a first preferred embodiment of an apparatus for ablating tissue using electrical energy, including a cannula and an array of electrodes deployable from the cannula.

FIG. 2 is a detail of the distal end of the cannula shown in FIG. 1, showing the array of electrodes in a collapsed configuration within the cannula.

FIG. 3 is a detail of the distal end of the cannula shown in FIG. 1, showing an alternative array of electrodes deployed from the cannula.

FIG. 4 is a cross-sectional view of a float valve for use with the apparatus of FIG. 1.

FIGS. 6A-6C are side views of a second preferred embodiment of an apparatus for ablating tissue using electrical energy, including a cannula and an opposing pair of jaw-like electrodes deployable from the cannula.

DETAILED DESCRIPTION OF THE ILLUSTRATED EMBODIMENTS

Figure 5A:
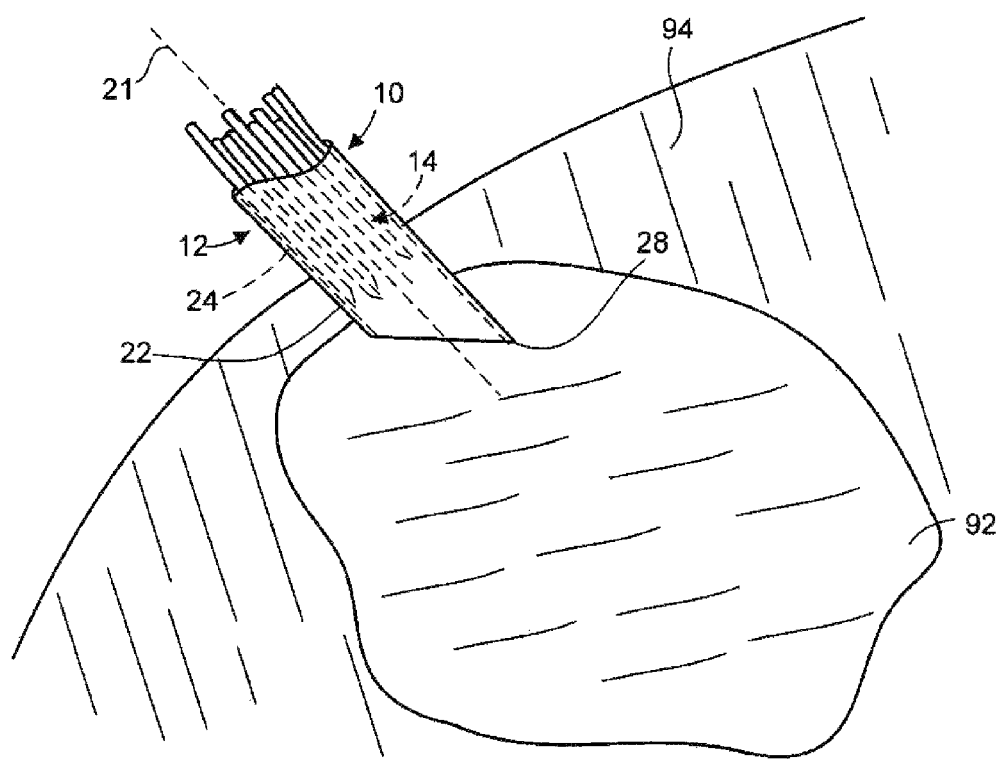
FIGS. 5A and 5B are cross-sectional views of a tissue structure, showing a method for treating a tumor within the tissue structure using the apparatus of FIG. 1.

Turning to the drawings, FIGS. 1-4 show a first preferred embodiment of an apparatus 10 for treating tissue, such as a benign or malignant tumor within a tissue structure (not shown). Generally, the apparatus 10 includes a cannula or other introducer 12 and an array of electrodes 14 deployable from the cannula 12. In addition, the apparatus 10 may include a source of electrical energy 16 and/or a source of conductive fluid 18 coupled to the array of needles 14.

The cannula 12 is an elongate tubular member including proximal and distal ends 20, 22 and a lumen 24 therein extending proximally from a distal port 26 towards the proximal end 20, thereby defining a longitudinal axis 21. The lumen 24 may extend to the proximal end 20, although the proximal end 20 may be substantially closed as shown. Alternatively, the lumen 24 may extend to a proximal port (not shown) in the proximal end 20 for removably receiving instruments, e.g., the array of electrodes 14 or a stylet (not shown), therethrough. The cannula 12 may also include a handle 25 on the proximal end 20 to facilitate manipulation of the cannula 12 and/or the array of electrodes 14.

The cannula 12 may be formed from a substantially rigid material, such as metal or plastic, and/or may be formed from an electrically insulating material. The distal end 22 of the cannula 12 may terminate in a sharpened or tissue-penetrating tip, e.g., a beveled tip 28 (not shown, see FIGS. 5A and 5B) to facilitate advancing the cannula 12 through tissue. Alternatively, the cannula 12 may be formed from a semi-rigid or flexible material, and a stylet (not shown) may be introduced into the lumen 24 from a proximal port (not shown). The stylet may enhance a rigidity of the cannula 12, and/or may include a sharpened distal tip (also not shown) that may extend beyond the distal end 22 of the cannula 12 to facilitate advancing the cannula 12 through tissue.

The array of electrodes 14 includes a plurality of elongate needles 30, each of which includes a proximal end 31 and a sharpened or tissue-penetrating distal tip, e.g., a beveled tip 32. At least one of the needles 30, and optionally all of the needles 30, may include an infusion lumen 34 for delivering a fluid to an outlet 36 in its distal tip 32. Alternatively, the needle(s) 30 may include multiple outlets (not shown) in the distal tip(s) 32, e.g., for delivering fluid in a predetermined pattern beyond the distal tip(s) 32. The needles 30 extend proximally through the lumen 24 of the cannula 12 and the proximal ends 31 may be connected to a hub 38, which may include a side port 40 communicating with the infusion lumen(s) 34 of the needle(s) 30.

A fluid line 42 may extend from the side port 40 to the source of conductive fluid 18 for delivering electrically conductive fluid, e.g., hypertonic saline, into the infusion lumen(s) 34 of the needle(s) 30. The source of conductive fluid 18 may include a manual source of conductive fluid, such as a syringe (not shown), or may include a pump (not shown) for continuously or intermittently delivering saline during a procedure. The fluid line 42 may include a relief valve 44 for maintaining the pressure of fluid being delivered via the fluid line 42 below a predetermined pressure. For example, the relief valve 44 may open at the predetermined pressure to prevent the patient from being exposed to excessive fluid pressures.

In addition, the fluid line 42 may include a float valve 46, such as that shown in FIG. 4, for ensuring that only liquids, such as saline, are delivered via the needles 30. For example, the float valve 46 may include a hydrophobic membrane 48 covering a reservoir 50 through which gases, such as air, may pass freely. Thus, fluid leaving the reservoir 50 may be substantially free from air bubbles that may otherwise cause injury if released within a patient's body, e.g., into a patient's vasculature.

With particular reference to FIGS. 1 and 2, the array of electrodes 14 may be movable from a collapsed configuration, e.g., when retracted into the lumen 24 of the cannula 12 (see FIG. 2), to an expanded configuration, e.g., when extended beyond the distal end 22 of the cannula 12 (see FIG. 1). Preferably, the needles 30 are biased to expand towards the expanded configuration, but may be resiliently compressed into the collapsed configuration when withdrawn into the lumen 24 of the cannula 12. In a preferred embodiment, the needles 30 are formed from an elastic or superelastic material, e.g., stainless steel or Nitinol, that may be sufficiently strong and biased to expand towards the expanded configuration even as the needles 30 are advanced through tissue.

Distal portions 33 of the needles 30 may expand such that the array of electrodes 14 defines a generally symmetrical shape, e.g., an umbrella or everted shape, as shown in FIG. 1. In one embodiment, the array of electrodes 14 may generally define a plane, as disclosed in U.S. Pat. Nos. 6,050,992 and 6,212,433. The disclosures of these references and any others cited therein are expressly incorporated herein by reference. Alternatively, as shown in FIG. 3, some of the needles 30', 30" may have different lengths than others and/or may have different radii of curvature to which they are biased. When fully deployed, as shown, the distal portions 33', 33" of the needles 30', 33" may extend different axial distances from the distal end 22 of the cannula 12 and/or may extend different radial distances from the longitudinal axis 21 in the expanded configuration. Thus, the array of electrodes 14' may define a generally spherical or other three-dimensional configuration when extended into the expanded configuration. This configuration may enhance treatment of a larger target tissue region, as explained further below.

The distal portion(s) 33 of one (or more) of the needle(s) 30 may include an electrode for delivering electrical energy to tissue adjacent the distal tip(s) 32. In one embodiment, each of the needles 30 may be formed from an electrically conductive material, such as stainless steel or Nitinol. Thus, the entire exposed distal portions 33 of the needles 30 extending beyond the distal end 24 of the cannula 12 may define electrodes. In this embodiment, the cannula 12 may be formed from an electrically insulating material. Alternatively, the needles 30 may be formed from electrically insulating material, e.g., plastic, and may include one or more electrically conductive regions (not shown) on the distal portions 33 that define electrodes. In this alternative, the needles 30 may include wires or other conductors (not shown) extending proximally from the electrodes, e.g., within the needles 30 to their proximal ends 31.

The needles 30 may be electrically coupled to the source of electrical energy 16, preferably a radio frequency (RF) generator, for delivering electrical energy to the distal portions 33 of the needle(s) 30. The RF generator 16 may be coupled to the proximal end 20 of the cannula 12 and/or to the hub 38, e.g., by a cable (not shown), which may, in turn, be coupled to the proximal end(s) 31 of the needles 30.

The RF generator 16 may be configured for delivering RF energy in a monopolar or a bipolar mode. In a monopolar mode, all of the needles 30 may be coupled to one pole of the RF generator 16. A passive electrode (not shown) may be provided that may be coupled to an opposite pole of the RF generator 16. Preferably, the passive electrode is a pad (not shown), e.g., having a relatively large surface area compared to the distal portions 33 of the needles 30, that may be placed against an outer surface of a patient being treated.

Alternatively, in bipolar mode, some of the needles 30 may be coupled to one pole, while other needles 30 may be coupled to the opposite pole. In another alternative, all of the needles 30 may be coupled to one pole, and an electrode (not shown) may be provided on the distal end 24 of the cannula 12 that may be coupled to the opposite pole. In yet a further alternative, all of the needles 30 may be coupled to one pole, and an internal surface electrode (not shown) may be coupled to the opposite pole that may be placed in contact with a surface of the tissue structure being treated. Such a surface electrode is disclosed in U.S. Pat. No. 6,212,433 incorporated by reference above.

Figure 5B:
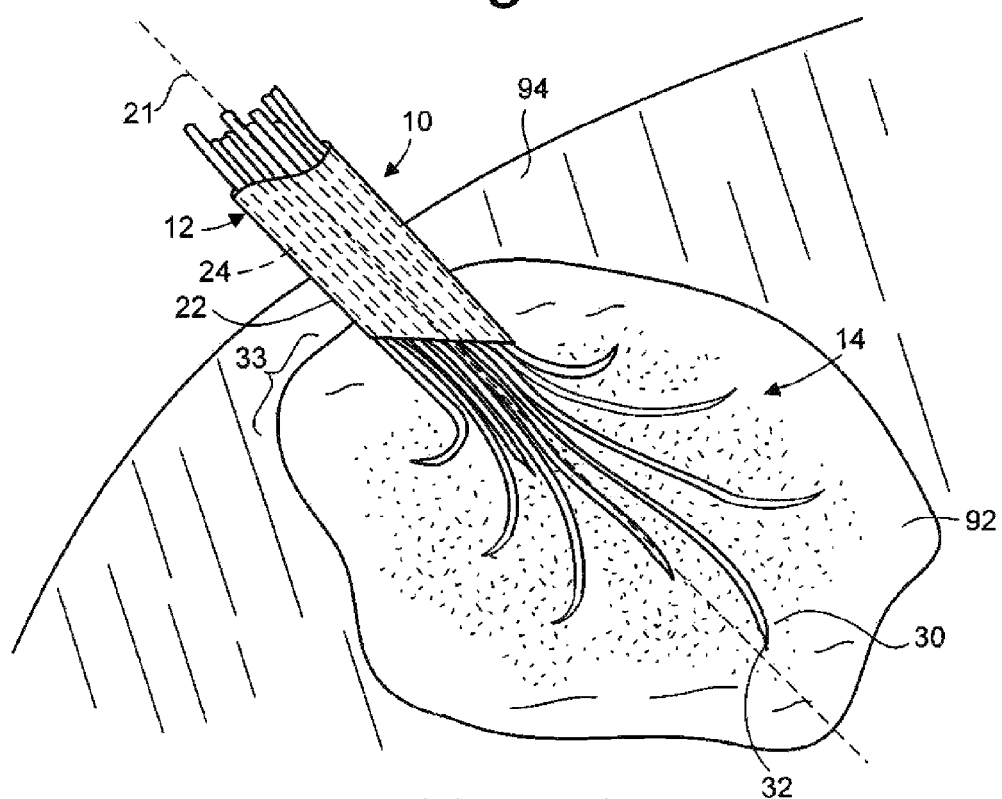

Turning to FIGS. 5A and 5B, the apparatus 10 may be used to treat a variety of soft tissues, e.g., to heat and/or ablate a benign or malignant tumor. For example, the apparatus 10 may be used to treat tumors within organs or other tissue structures, such as a liver, kidney, pancreas, stomach, spleen, prostate, breast, and lung.

Initially, the array of electrodes 14 may be provided within the lumen 24 of the cannula 12, i.e., in the collapsed configuration. The distal end 22 of the cannula 12 may be advanced into a target tissue region 92 of a patient that is to be treated. For example, a surgical procedure may be used to expose a tissue structure 94, e.g., a liver or other organ, having a tumor or other target region 92 therein. The sharpened distal tip 28 of the cannula 12 may be inserted into the tissue structure 94 until the distal end 22 is disposed within or adjacent to the target region 92, as shown in FIG. 5A. Alternatively, it may be possible to insert the cannula 12 directly through the patient's skin, any intervening tissue (not shown), and into the tissue structure 94, without requiring a procedure to expose the tissue structure 94.

The cannula 12 may be manipulated while using external imaging, such as MRI, fluoroscopy, and the like, to place the distal end 24 in a predetermined position relative to the target tissue region 92. For example, the distal end 22 of the cannula 12 and/or the needles 30 may include markers, e.g., radiopaque markers, that may facilitate identifying the location of the cannula 12 using external imaging.

If the cannula 12 is flexible or does not include a sharpened distal tip, the cannula 12 may be advanced through an introducer (not shown) previously placed into the target tissue region 92. Alternatively, a stylet (not shown) may be inserted into the proximal end 20 (e.g., without the array of electrodes 14 in the cannula 12) and advanced until a sharpened distal tip (also not shown) of the stylet extends beyond the distal end 22 of the cannula 12. The sharpened tip of the stylet may then be used to penetrate and guide the cannula 12 into the tissue structure 94. Once the distal end 22 of the cannula 12 is properly positioned, the stylet may be removed, and the array of electrodes 14 may be introduced into the lumen 24 of the cannula 12.

The array of electrodes 14 may be advanced from the distal end 22 of the cannula 12 and into the tissue structure 94. Preferably, the needles 30 have sufficient column strength to pass through the tissue without buckling or deflecting in an unpredictable manner. The sharpened distal tips 32 may expand automatically due to the inherent bias of the needles 30 to adopt the expanded configuration, such as that shown in FIG. 5B. The deployment of the array of electrodes 14 may also be monitored using external imaging to ensure that the needles 30 expand as desired within the target region 92.

With the array of electrodes 14 deployed within the target region 92, saline (or other conductive fluid) may be introduced into the target region 92 via the outlets 36 communicating with the infusion lumens 34 (not shown in FIG. 5B). Saline may be delivered in a single bolus, continuously, or intermittently during the treatment. The amount of saline introduced may be adjusted to maximize heat transfer, while minimizing adverse effects that may result from excessive volumes of saline, such as cooling of the electrodes and/or excessive saline delivery into the patient's body, as will be appreciated by those skilled in the art.

The RF generator 16 (not shown in FIG. 5B) may then be activated, thereby delivering RF energy to the distal portions 33 of the needles 30, and, consequently, to the surrounding tissue in the target region 92. Due to the presence of the saline, the amount of heat transferred to the target region 92 may be substantially enhanced, causing a larger region of tissue to be heated and necrosed as compared to a similar power level of RF energy without saline. This is because the saline may provide a larger supply of electrons than the tissue alone (without the saline), thereby substantially increasing the electrical conductivity of the tissue and allowing the RF energy to flow deeper into the tissue.

If the RF generator 16 is operated in a monopolar mode, a passive electrode (not shown) may be coupled to the patient, e.g., to a region of the patient's skin (not shown). Preferably, the passive electrode has a sufficiently large contact area such that the tissue contacted by the passive electrode is not heated excessively. Alternatively, the RF generator 16 may be operated in a bipolar mode such that a heated region is created between the electrodes, as explained in the references incorporated by reference above.

If the array of electrodes 14 includes needles 30 having different lengths and curvatures, as shown in FIGS. 4 and 5B, the distal tips 32 may extend different axial and radial distances into the tissue within the target region 92. Consequently, the array of electrodes 14 may expand into a generally spherical or other three-dimensional shape that may substantially occupy the target region 92. When saline is introduced via the needles 30, the saline may be injected more extensively and/or uniformly through the target region 92, e.g., within a larger three-dimensional volume. Thus, when RF energy is delivered into the target region 92, the increased perfusion of saline may enhance heating of the tissue within the target region 92. This may result in a larger and more uniform three-dimensional volume being necrosed by the array of electrodes 14, and/or may reduce the RF delivery time necessary to ablate tissue within the target region 92.

Turning to FIGS. 6A-6C, another preferred embodiment of an apparatus 110 is shown that includes a cannula 112 and a pair of jaw-like electrodes or opposing members 114 extendable from the cannula 112. In addition, the apparatus 110 may include a source of electrical energy and/or a source of conductive fluid (not shown) that may be coupled to the pair of electrodes 114, similar to the embodiment described above.

The cannula 112 generally includes a proximal end 120, a distal end 122, and a lumen 124 extending between the proximal and distal ends 120, 122, thereby defining a longitudinal axis 121. The cannula 112 may be a substantially rigid tubular member including a sharpened distal tip 128, similar to the embodiment described above. Alternatively, a flexible tubular member, such as a catheter (not shown), may be provided instead of the cannula 112 that includes a substantially blunt or rounded distal tip (also not shown). In this alternative, the distal end of the catheter may have a size and/or shape to facilitate substantially atraumatically advancing the apparatus through a body lumen or other passage (not shown).

The pair of electrodes 114 include first and second elongate members or "jaws" 130 including proximal and distal ends 131, 132 and defining inner surfaces 134 that are oriented generally towards one another. The jaws 130 may be pivotally connected to one another at their proximal ends 131 such that the distal ends 132 may be movable away from and towards one another. Preferably, the jaws 130 are resiliently compressible towards one another to define a collapsed configuration, as shown in FIG. 6A, but are biased to move away from one another towards an expanded configuration, as shown in FIG. 6C. The jaws 130 may be biased to assume an arcuate shape, e.g., as shown in FIG. 6C, although, alternatively, the jaws 130 may be biased to a substantially straight shape (not shown), e.g., such that the pair of electrodes 114 130 define a "V" shape in the expanded configuration.

At least one, and preferably each, of the jaws 130 includes a plurality of hollow needles 136 extending from the inner surfaces 134, i.e., towards the opposing jaw 130. The needles 136 include sharpened or tissue-penetrating tips 138, e.g., beveled or pointed tips, that include outlets 140 communicating with a lumen 142 within the respective jaw 130. The lumen 142 may extend proximally from the distal-most needle 136 of the respective jaw 130 to the proximal end 131. Optionally, the distal end(s) 132 of the jaw(s) may include a sharpened tip and/or may include an outlet (not shown) communicating with the lumen 142. Alternatively, the distal end(s) 132 may be blunt or rounded (not shown) to prevent the distal end(s) 132 from penetrating tissue, as explained further below.

In addition, one or both jaws 130 include one or more electrodes for delivering electrical energy to tissue engaged between the jaws 130. For example, the jaws 130 may be formed from electrically conductive material, e.g., stainless steel or Nitinol, such that the entire exposed surface of the jaws 130 defines an electrode. Alternatively, the jaws 130 may be formed from electrically insulating material, e.g., plastic, and the needles 136 and/or the inner surface(s) 134 of the jaw(s) 130 may be formed from conductive material or may be coated with a conductive material. In this alternative, conductors, e.g., wires or conductive deposits (not shown), may be provided on or in the jaws 130 for delivering electrical energy to the needles 136 and/or the inner surface(s) 134. The conductors may be provided in separate lumens (not shown) within the jaws 130 or may be deposited to a surface of the jaws 130 and covered with an insulating material.

The pair of electrodes 114 may be provided on a distal end 144 of an elongate member, e.g., a tubular member 146, including an infusion lumen 148 communicating with the lumens 142 in each of the jaws 130. Preferably, the tubular member 146 has sufficient column strength to provide a control element for moving, i.e., pushing and pulling, the pair of electrodes 114 axially with respect to the cannula 112. For example, the tubular member 146 may extend into the lumen 124 of the cannula 112 such that the tubular member 146 is slidable axially relative to the cannula 112.

A proximal end (not shown) of the tubular member 146 may be coupled to an actuator and/or handle on the proximal end (also not shown) of the cannula 112. Thus, movement of the actuator or handle may direct the tubular member 146 axially within the lumen 124. Preferably, axial movement of the tubular member 146 is used to deploy the pair of electrodes 114 from within the lumen 124 and/or to withdraw the pair of electrodes 114 into the lumen 124. For example, the tubular member 146 may be pulled proximally such that the jaws 130 are resiliently compressed towards one another as they are with drawn into the lumen 124 of the cannula, as shown in FIG. 6A. When the tubular member 146 is pushed distally, as shown in FIGS. 6B and 6C, the jaws 130 may automatically return towards the expanded configuration.

The jaws 130 may be formed from an elastic or superelastic material, similar to the previous embodiment, that may facilitate expansion and/or resilient compression of the jaws 130. Alternatively, the jaws 130 may be mechanically steerable such that the jaws 130 may be selectively directed away from one another towards the expanded configuration. The pair of electrodes 114 may be formed as a single piece or may be multiple pieces, e.g., separate jaws 130 that may be attached to one another. The pair of electrodes 114 may be connected to the distal end 144 of the tubular member 146, e.g., such that the tubular member 146 and the pair of electrodes 114 are substantially permanently attached to one another. Alternatively, the pair of electrodes 114 and the tubular member 146 may be formed as a single part. In any of these embodiments, conventional manufacturing and assembly methods may be used, as will be appreciated by those skilled in the art.

Similar to the previous embodiment, a source of saline or other conductive fluid (not shown) may be connected to the proximal end of the tubular member 146 such that saline may be delivered via the infusion lumen 148 into the lumens 142 of the jaws 130 and through the outlets 140 in the needles 136. In addition, a source of electrical energy, e.g., an RF generator (not shown), may be coupled to the pair of electrodes 114, e.g., by a cable connected to the proximal end (also not shown) of the cannula 112 and/or the tubular member 146.

Turning to FIGS. 7A-7D, the apparatus 110 may be used to heat and/or ablate tissue within a patient, similar to the previous embodiment. The apparatus 110 may be particularly useful for ablating a tumor or other tissue at or near a surface of an organ or other soft tissue structure, such as a liver, kidney, pancreas, stomach, spleen, lung, prostate, breast, and the like. Initially, the pair of electrodes 114 may be provided in the collapsed configuration, e.g., within the lumen 124 of the cannula 112 as shown in FIG. 6A.

Figure 7A:
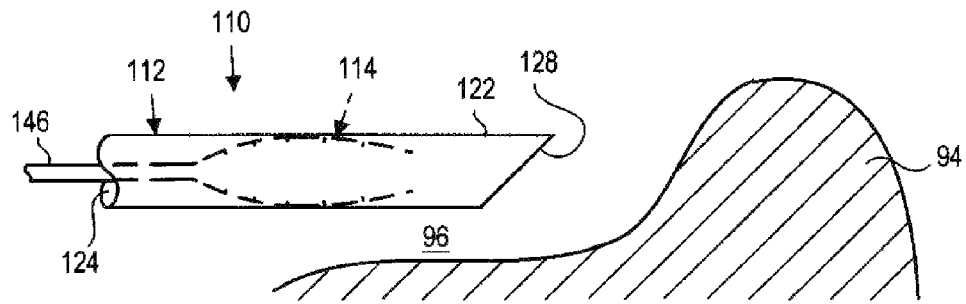
FIGS. 7A-7D are cross-sectional views of a tissue structure, showing a method for treating a tumor within the tissue structure using the apparatus of FIGS. 6A-6C.

With particular reference to FIG. 7A, with the pair of electrodes 114 collapsed, the distal end 122 of the cannula 112 may be introduced into a space 96 adjacent a tissue structure 94 within a patient that is to be treated. If the cannula 112 is substantially rigid and includes a sharpened distal tip 128, the cannula 112 may inserted directly into the patient's skin or an outer surface of an organ, through any intervening tissue, and into the space 96. Alternatively, the cannula 112 may be advanced through tissue using an internal stylet (not shown), similar to the embodiment described above. The stylet may be removed and then the pair of electrodes 114 may be advanced through the lumen 124 of the cannula 112 to the distal end 122.

In a further alternative, a flexible outer tubular member instead of a rigid cannula 112 may be used. The distal end 122 of the outer tubular member may be advanced along a natural body passage (not shown) into the space 96. For example, the distal end 122 may be advanced over a guidewire or other rail (not shown) already positioned within the space 96 using known methods.

Figure 7B:
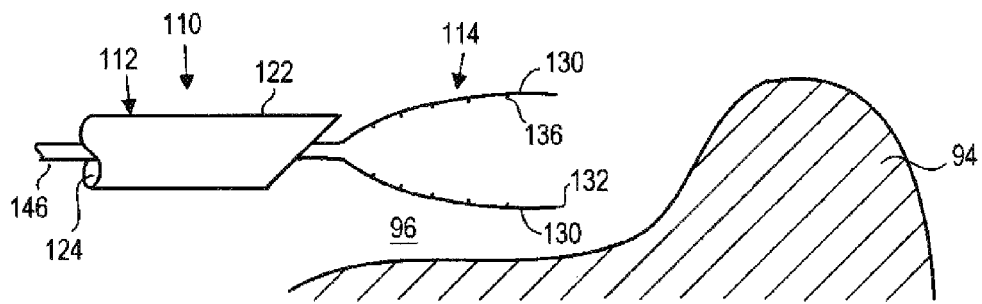

Turning to FIG. 7B, the pair of electrodes 114 may be deployed from the cannula 112, and the jaws 130 may be directed away from one another to the expanded configuration. For example, the distal end 122 of the cannula 112 may be retracted relative to the pair of electrodes 114, or the pair of electrodes 114 may be advanced distally relative to the cannula 112. Preferably, the jaws 130 are biased to move away from one another automatically upon deployment from the distal end 122 of the cannula 112, although alternatively, the jaws 130 may be mechanically expanded away from one another, as explained above.

Figure 7C:
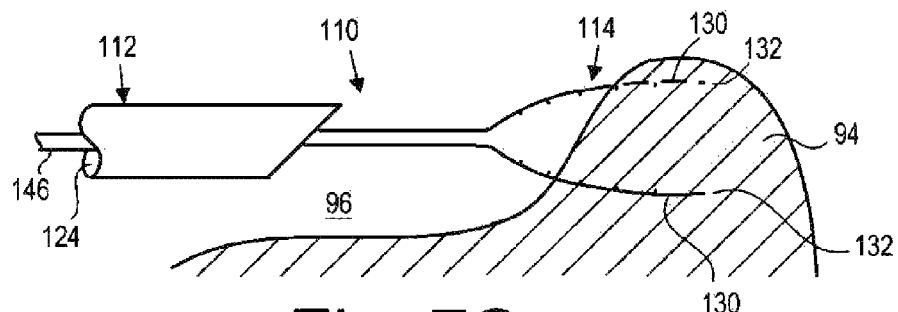
Figure 7D:
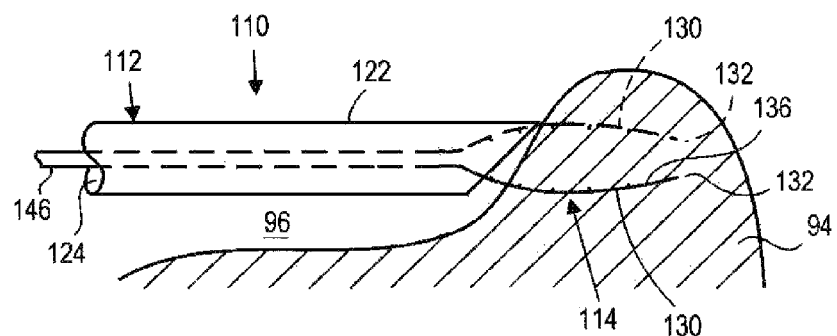

As shown in FIG. 7C, the pair of electrodes 114 may be manipulated, e.g., advanced until the tissue structure 94 is disposed between the jaws 130. The jaws 130 may then be directed towards one another to engage the tissue structure 94 between inner surfaces 134 of the jaws 130, as shown in FIG. 7D. Preferably, the jaws 130 are forced together by advancing the distal end 122 of the cannula 112 distally towards the tissue structure 94 such that the jaws 130 begin to enter the lumen 124. As the proximal ends of the jaws 130 are directed towards one another, the bias of the jaws 130 may be overcome, forcing the distal ends 132 of the jaws 130 towards one another. Because of the sharpened tips 138 of the needles 136, this action may cause the needles 136 to penetrate and enter at least partially into the tumor 92 in the tissue structure 94.

Saline or other conductive fluid may be injected from a source (not shown) via the needles 130 into the tissue structure 94. The saline may be injected in a single bolus, intermittently, or continuously during the procedure, similar to the previous embodiment. The RF generator (not shown) may be coupled to the pair of electrodes 114, and RF electrical energy may be delivered via the needles 130 and or the inner surface(s) of the jaws 130 into the tissue structure 94 to ablate all or a portion of the tissue structure 94.

Once sufficient RF energy is delivered, the pair of electrodes 114 may be expanded, e.g., by partially withdrawing the cannula 112 (similar to that shown in FIG. 7C). If desired, the pair of electrodes 114 may be manipulated to another portion of the tissue structure 94 (not shown), and the procedure repeated to ablate additional tissue within the tissue structure 94. Finally, the pair of electrodes 114 may be withdrawn away from the tissue structure 94 and/or withdrawn into the cannula 112, and the cannula 112 may be removed from the patient.

In embodiments of the invention, the needles are generally elongate rods or tubes formed from an electrically conductive and porous material, e.g., sintered stainless steel, thereby providing an electrode through which electrolytic fluid may flow for delivering electrical energy to tissue surrounding the needle. The needles may be rigid or flexible, and/or may be straight or biased to a curved shape. A range from a single needle to an array of needles deployable into an expanded three-dimensional configuration, such as the configuration shown in FIGS. 1-4 and described above, may be employed.

In selected embodiments, the needles may be formed as an extruded or cast sintered rod. A beveled or sharpened distal tip may be ground or otherwise formed. Thus, the entire needle may be porous such that fluid introduced into the proximal end of the needle may flow through the pores and exit an exposed distal portion of the needle. Additionally or alternatively, the needles may be a co-extruded sintered tube, including an infusion lumen for delivering a fluid to an outlet in its distal tip. Thus, some of the fluid passing through the lumen may weep through the pores of the needle and exit the needle, while the remaining fluid may exit the outlet. In a further alternative, a lumen may extend partially into the needle from the proximal end, but not completely to is distal tip.

An advantage of using a sintered/porous material to form the needle(s) is that visibility of the distal portion of the needle(s) under certain imaging modalities may be enhanced. For example, the sintered/porous material may substantially increase the echogenicity of the needle when using ultrasound imaging. Thus, the distal portion may be monitored to ensure that a desired length of the needle is advanced from the introducer sleeve into the target tissue structure. If a plurality of needles are provided, each of the needles may be formed from sintered/porous material, thereby facilitating monitoring deployment of the array within the tissue structure.

Once the needle(s) are deployed, saline or other conductive fluid may be injected from a source via the needle into the tissue structure. The saline may be injected in a single bolus, intermittently, or continuously during the procedure, as described herein. Because of the porous nature of the sintered material, the saline may more uniformly permeate the surrounding tissue as compared with a needle including a lumen having only one or more discrete outlets. Once sufficient RF energy is delivered, the needle(s) are at least partially withdrawn into the introducer sleeve, and the sleeve is removed from the patient and/or moved to another location to ablate additional tissue.

While the invention is susceptible to various modifications, and alternative forms, specific examples thereof have been shown in the drawings and are herein described in detail. The invention is not limited to the particular embodiments or methods disclosed, but is to include all modifications, equivalents and alternatives falling within the scope of the appended claims.

What is claimed:

1. An apparatus for delivering electrical energy to tissue within a patient, comprising:
  a tubular member comprising a proximal end, a distal end having a size for insertion into a body of a patient, and a lumen extending between the proximal and distal ends of the tubular member;
  a pair of opposing members extendable from the distal end of the tubular member, the opposing members being expandable away from one another and being directable towards one another for engaging tissue between inner surfaces of the opposing members, the opposing members comprising one or more electrodes for delivering electrical energy to tissue engaged between the opposing members;
  one or more hollow needles extending from an inner surface of at least one opposing member, each needle comprising a sharpened tip for penetrating tissue engaged between the opposing members and an outlet in the sharpened tip communicating with a lumen in the opposing member for delivering conductive fluid from the lumen into tissue penetrated by the sharpened tip;
  a control member extending through the lumen of the tubular member, wherein the opposing members extend from the control member, and wherein the opposing members are directable towards one another by directing the control member proximally to at least partially withdraw the opposing members into the lumen, the control member having an infusion lumen therein communicating with the outlet of the needle via the lumen in the opposing member; and a source of conductive fluid communicating with the infusion lumen for delivering conductive fluid to the outlet of the needle, the source of conductive fluid connected to a valve for removing gases from conductive fluid being delivered from the source of conductive fluid to the outlet of the needle.

2. The apparatus of claim 1, wherein the inner surfaces of the opposing members comprise electrically conductive material defining the electrodes.

3. The apparatus of claim 1, wherein the one or more electrodes comprises one or more electrodes coupled to a first terminal of a source of electrical energy and one or more electrodes coupled to a second terminal of the source of electrical energy such that the apparatus is operated in a bipolar mode.

4. The apparatus of claim 1, wherein the tubular member comprises a substantially rigid cannula, and wherein the distal end comprises a sharpened distal tip for penetrating tissue.

5. The apparatus of claim 1, further comprising a substantially rigid cannula including a sharpened distal tip for penetrating tissue, and wherein the tubular member is insertable through the cannula when the opposing members are withdrawn into the tubular member.

6. The apparatus of claim 1, where the source of conductive fluid comprising a reservoir and a hydrophobic membrane covering the same.

7. The apparatus of claim 1, wherein the opposing members comprise an elastic or superelastic material.

8. The apparatus of claim 7, wherein the opposing members comprise stainless steel.

9. The apparatus of claim 7, wherein the opposing members comprise a shape memory alloy.

10. The apparatus of claim 7, wherein the opposing members comprise an electrically insulating material with one or more electrically conductive regions.

11. The apparatus of claim 10, wherein the one or more electrically conductive regions comprise wires.

* * * * *